US010513064B2

(12) United States Patent
Newman et al.

(10) Patent No.: US 10,513,064 B2
(45) Date of Patent: Dec. 24, 2019

(54) PROCESS AND APPARATUS FOR MAKING MULTI-COMPONENT HOLLOW ARTICLE AND ARTICLE MADE THEREBY

(71) Applicant: The Procter & Gamble Company, Cincinnati, OH (US)

(72) Inventors: Mattthew Lloyd Newman, Cincinnati, OH (US); Uwe Jungnickel, Koenigstein/Taunus (DE); Benedikt Heil, Friedberg (DE); Joerg Kotitschke, Waldems (DE); Andreas Reuschenbach, Bad Soden (DE); Andreas Bresselschmidt, Weiterstadt (DE); Holger Schulz, Frankfurt am Main (DE); Jochen Ganninger, Eschborn (DE); John Carson, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1101 days.

(21) Appl. No.: 14/135,030

(22) Filed: Dec. 19, 2013

(65) Prior Publication Data
US 2015/0174802 A1 Jun. 25, 2015

(51) Int. Cl.
*B29C 45/00* (2006.01)
*A46B 9/04* (2006.01)
(Continued)

(52) U.S. Cl.
CPC ............ *B29C 45/0003* (2013.01); *A46B 9/04* (2013.01); *A61C 17/16* (2013.01);
(Continued)

(58) Field of Classification Search
CPC ............ B29C 45/0003; B29C 45/2602; B29C 45/1675; B29C 45/1704;
(Continued)

(56) References Cited

U.S. PATENT DOCUMENTS 5,028,377 A 7/1991 Watson
6,645,587 B1 11/2003 Guergov
(Continued)

FOREIGN PATENT DOCUMENTS

DE 19500138 7/1996
JP H0329309 3/1991
(Continued)

OTHER PUBLICATIONS

Machine translation of JP08-057887 (Year: 1996).*
International Search Report and Written opinioin, dated Feb. 23, 2015; 11 pages.

*Primary Examiner* — Robert J Grun
(74) *Attorney, Agent, or Firm* — Parker D. McCrary; Vladimir Vittenberg

(57) ABSTRACT

An injection-molding process and an apparatus for making a multi-component hollow article, and the article made thereby. The process comprises molding, from a first plastic material, a hollow body having a wall with at least one vent therethrough and at least one flap molded in an area adjacent to the vent. The flap is molded in a first position in which the vent is open. The flap is hingedly movable from the first position to a second position in which the vent is closed by the flap. After the flap is folded into the second position, the hollow body, including the folded flap, is at least partially overmolded with a second plastic material, wherein the second material is essentially precluded from leaking into the hollow body through the vent. The apparatus comprises a first mold bar for molding a hollow body, a second mold bar for overmolding the hollow body with a second plastic material, and a closing tool for moving, and optionally retaining, the flap in the second position. The resulting article has no second material inside its hollow body.

11 Claims, 18 Drawing Sheets

(51) Int. Cl.
  *A61C 17/16* (2006.01)
  *B29C 45/26* (2006.01)
  *B29C 45/16* (2006.01)
  *B29C 45/17* (2006.01)
  *B29K 101/00* (2006.01)
  *B29L 31/42* (2006.01)

(52) U.S. Cl.
  CPC ...... *B29C 45/1675* (2013.01); *B29C 45/1704* (2013.01); *B29C 45/2602* (2013.01); *B29C 2045/1693* (2013.01); *B29C 2045/1718* (2013.01); *B29C 2045/1787* (2013.01); *B29K 2101/00* (2013.01); *B29L 2031/425* (2013.01)

(58) Field of Classification Search
  CPC .... B29C 2045/1693; B29C 2045/1718; B29C 2045/1787; A46B 9/04; A61C 17/16; B29K 2101/00; B29L 2031/425
  See application file for complete search history.

(56) References Cited

U.S. PATENT DOCUMENTS

| | | |
|---|---|---|
| 2012/0291885 A1 | 11/2012 | Altonen et al. |
| 2012/0292823 A1 | 11/2012 | Altonen et al. |
| 2012/0294963 A1 | 11/2012 | Altonen et al. |
| 2012/0295049 A1 | 11/2012 | Altonen et al. |
| 2012/0295050 A1 | 11/2012 | Altonen et al. |
| 2013/0069280 A1 | 3/2013 | Altonen et al. |
| 2013/0113131 A1 | 5/2013 | Altonen et al. |
| 2013/0221572 A1 | 8/2013 | Berg, Jr. et al. |
| 2013/0221575 A1 | 8/2013 | Altonen et al. |

FOREIGN PATENT DOCUMENTS

| | | |
|---|---|---|
| JP | H06270182 | 9/1994 |
| JP | H0857887 | 3/1996 |
| JP | H08267504 | 10/1996 |

* cited by examiner

PROCESS AND APPARATUS FOR MAKING MULTI-COMPONENT HOLLOW ARTICLE AND ARTICLE MADE THEREBY

FIELD OF THE INVENTION

The invention is directed to a process and an apparatus for manufacturing a multi-component hollow article by injection molding, and an article made by such process and apparatus. More particularly, the invention is concerned with manufacturing a hollow article comprising at least two plastic materials by an injection-molding process involving overmolding of a hollow component comprising one plastic material with another plastic material so that the overmolding plastic material is essentially precluded from penetrating into the hollow component.

BACKGROUND OF THE INVENTION

Injection molding has been well known and widely used in constructing relatively complex plastic parts, including those having empty space or spaces inside. Examples include plastic bodies of various tools, instruments, medical equipment, and personal-care implements, such as, e.g., various toothbrushes, both manual and power, the latter commonly housing power source and drive mechanism inside a hollow plastic housing, typically comprising the toothbrush's handle. These articles may comprise multi-component plastic bodies that include two or more plastic materials: a first material forming a hollow body and a second material that is at least partially molded over the first material. With respect to both manual and power toothbrushes, it may be desirable to create a hollow plastic body comprising two or more plastic materials such that a hollow component comprising a first plastic material is overmolded, at least partially, by a second plastic material.

It is generally known to use a gas-assisted injection molding process to create hollow articles. See, e.g., U.S. Pat. No. 6,645,587. In a gas-assisted process, a hollow body, comprising a first plastic material, typically includes an opening, or vent, through which the gas can enter, and escape from, the hollow body being created. Other injection molding processes, both involving gas and not involving gas, may also technologically require a vent or vents in the hollow body being created. For example, in a liquid-assisted injection molding, where gas is commonly used to purge the liquid following the liquid-injection step, typically at least two vents may be needed, one for liquid and the other for gas.

It is also known, e.g., that in an injection-molded component formed by using a customary mold tool typically comprising two mold parts (or "halves") and a core, an opening or recesses used to create a hollow component can be formed by providing a slider or a pin retractable into one of the mold parts or the core. In such a configuration, a hollow component, comprising a first plastic material, can be created by using an opening unobstructed by the retractable pin. Then, the retractable pin can be moved in a position to close the opening, and a second plastic material can be applied to overmold the first-material component. Because the opening is closed by the pin, the second material is precluded from penetrating into the hollow component through the opening—as long as the pin is in place. But such a retractable pin, if removed before solidification of the second material, would not prevent the second material from leaking into the hollow component. And the removal of the retractable pin after solidification of the second material would result in the article still having the opening.

There is a need, therefore, to seal the opening, or vent, in the hollow body to eliminate, or at least significantly reduce, the risk of the subsequent, overmolding material penetrating through the opening into the void of the hollow body while the second material is being molded over a portion of the hollow body. The present disclosure is directed to a process and equipment for manufacturing a hollow article by injection molding, wherein some of the deficiencies of the commonly known methods, described above, are minimized. The present disclosure is also directed to a hollow article, such as, e.g., a plastic body of a toothbrush, comprising a hollow structure including a shell made from a first material overmolded by at least a second material.

SUMMARY OF THE DISCLOSURE

A process for making a hollow article by injection molding comprises, in essence, forming a hollow body from a first plastic material in a first mold bar—and then at least partially overmolding the hollow body with a second plastic material in a second mold bar. Each of the mold bars can comprise two mold parts, or "halves," which in operation form a mold cavity therebetween, into which a plastic material can be injected through at least one injection nozzle. Each of the mold bars may also have nozzles or inlets for injecting gas or liquid into the mold cavity—and outlets for evacuating those therefrom. The second mold bar can comprise one of the first bar's "halves." In other words, the solidified hollow body, molded in the first mold bar, does not need to be removed from the portion of the first mold bar in which the hollow body has been molded. Instead, one of the first mold's halves having the solidified hollow body residing therein, can engage a third mold part or "halve" to form the second mold bar having the second mold cavity, which is larger than the first mold cavity.

The hollow body can be molded in the first mold bar, using, for example, a conventional injection molding, a gas-assisted injection molding or a liquid-assisted injection molding. In an gas-assisted process, injecting the first plastic material into the first mold cavity can be followed by injecting the gas into the first plastic material in the first mold cavity to force the first plastic material to conform to a surface of the first molding cavity. The hollow body being molded in the first mold bar has at least one vent extending through the hollow body's wall. This vent provides fluid communication between the area inside the hollow body and the surrounding environment. In embodiments of the gas-assisted injection molding or the liquid-assisted injection molding, the at least one vent provides an inlet and an outlet for gas and/or liquid to enter and exit the mold cavity. This vent will remain temporarily open in the solidified hollow body.

The hollow body also has at least one relatively small flap molded in an area of the wall adjacent to the at least one vent. The flap can be formed by providing one of the mold parts comprising the first mold bar with a relatively small recess, or aperture, a so-called "flap aperture"—for receiving a relatively small amount of the first plastic material during injection molding. A solidified portion of this relatively small amount of the first plastic material, when is solidified, will form the flap. The flap is molded in a first position, in which the flap extends generally outwardly from the wall of the hollow body. While the flap is in the first position, the vent is open. The flap is constructed to have a living hinge at the flap's base, i.e., where the flap meets the wall. This living hinge allows the flap to move (fold or bend) from the first position to a second position, in which the flap covers the vent. The flap and the vent are sized and situated relative to one another such that the flap can be folded or bent to securely close the vent in the second position.

A closing tool, such as, e.g., a pin, can be used to contact the flap and to move the flap from the first position to the second position. The closing tool can also be used to hold the flap in the second position to secure a proper position of the flap during injection of the second plastic material over the hollow body. The closing tool's working surface, contacting the flap, can have any suitable shape, e.g., it can comprise a planar surface, an inclined surface, a curved surface, and any combination thereof. In one embodiment, the closing tool can be structured to be movable within the second mold cavity between a fully extended position and a fully retracted position. In such an embodiment the working surface of the tool can be beneficially configured to comprise a portion of a surface of the second mold cavity when the closing tool is in the fully retracted position. In addition, the closing tool can be biased against the body of the second mold cavity.

After the closing tool moves the flap into the second position, the flap substantially covers the vent. To provide for a proper folding/bending of the flap, the flap may beneficially be molded to have a designated bending zone comprising a certain bend thickness so that a bend radius, formed in the fully folded or bent flap, satisfies the conditions required for a maximal allowable strain in the bending zone without flap getting broken off as a result of its folding/bending. In one embodiment, e.g., the thickness of the flap in the bending zone divided by the bend radius is less than a maximal allowable strain of the first plastic material in the bending zone.

The flap, in combination with the vent, can be configured to flush with an area of the wall surrounding the vent when the flap is in the second position. Alternatively, the flap can be configured to overlap a portion of the wall surrounding the vent when the flap is in the second position. In either embodiment, the flap should be sized and configured to substantially preclude the second material from leaking through the at least one vent into the hollow body when the flap is in the second position. To this end, in some embodiments the flap can be structured to seal the vent.

In other embodiments, the flap's living hinge can be designed to ensure that the flap neither folds/bends sideways nor breaks off from the rest of the hollow body when the flap is being folded or bent. Also, the closing tool's working surface and a corresponding portion of the surface of the flap may be molded to comprise mating guide elements, e.g., mating grooves/channels and projections/ridges, which would assist the closing tool to more accurately place the flap over the vent. In other embodiments, the hollow body and the flap can be molded to include mating surface features to facilitate an accurate positioning of the flap in the second position. In further embodiments, both the hollow body's flap-contacting surface and the flap can include mating features structured and configured to lock the flap in the second position.

After the flap is moved into the second position, and the vent is securely closed, the second plastic material can be applied to the surface of the hollow body to at least partially overmold the hollow body including the folded flap. Because the flap, being in the second position, shields the vent's opening from the second material, the second material is essentially precluded from entering the void inside the hollow body through the vent.

The resulting multi-component hollow article, made by the process and equipment described herein, comprises a hollow body made of a first plastic material at least partially overmolded by a second plastic material. The article has a vent through the hollow body's wall securely covered by a flap made of the first plastic material. The article, therefore, has been precluded from having the second material leaked into the void inside the hollow body. Such a multi-component article can be used in a variety of products, such as, e.g., a body of a tufted article, a body of a medical-equipment tool, a body of an instrument (manual or power), and a body of a personal-care implement. The multi-component article can be particularly suitable for the production of manual or power toothbrushes.

BRIEF DESCRIPTION OF THE DRAWINGS

The embodiments set forth in the drawings are illustrative and exemplary in nature—and are not intended to limit the subject matter defined by the claims. The detailed description of the illustrative embodiments can be understood when read in conjunction with the drawings, where like structures are indicated with like reference numerals.

DETAILED DESCRIPTION

A multi-component article, e.g., a plastic body of a toothbrush, can be manufactured in at least three general steps. In the first step, a first molded article having an opening or a vent is created; in a second step, the vent in the first molded article is closed; and in the third step, a second plastic component is molded over at least a portion of the first molded article, including a portion having a closed vent. In operation, some of the steps, e.g., the second and third steps, can be combined, as will be explained herein below.

Figure 1:
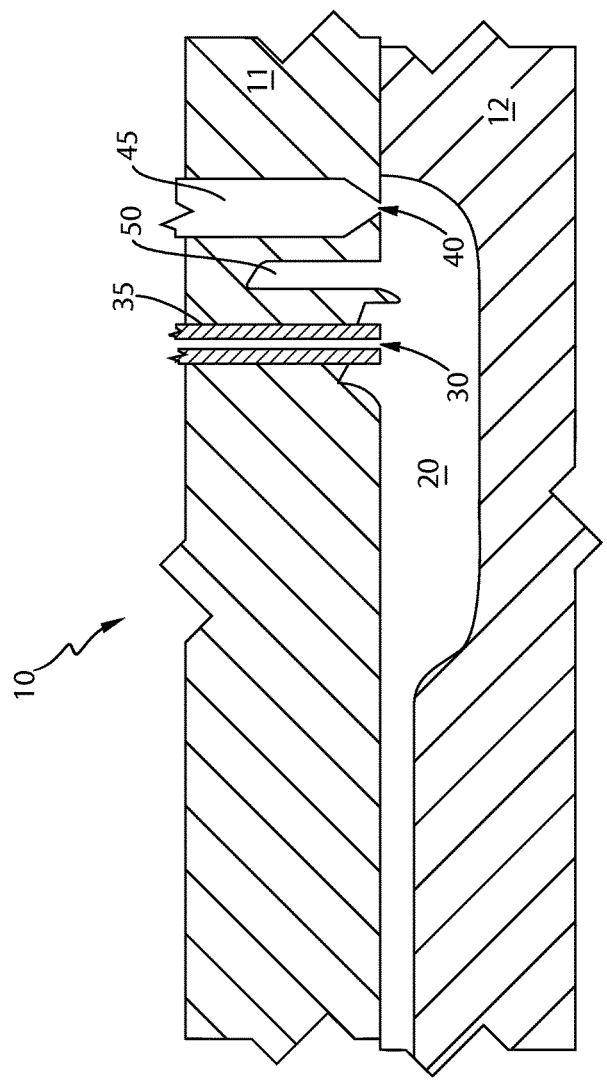
FIG. 1 shows a partial cross-sectional view of an embodiment of a first mold bar and schematically illustrates an embodiment of the process and equipment for constructing a hollow body having a vent and a flap structured and configured to close the vent.

In several exemplary embodiments of the current invention, shown in FIGS. 1-17, and disclosed, without limitation, in the context of a gas-assisted process and apparatus, a first mold cavity 20 can be formed between two mold parts, or "halves": a first mold part 11 and a second mold part 12, forming a first mold bar. At least one of the first and second mold parts 11, 12 of the first mold bar is configured to include at least one plastic-injection channel 35 terminating with a plastic-injection nozzle 30, through which a first plastic material 15 can be injected into the first mold cavity 20, and at least one fluid-injection channel terminating with a fluid-injection nozzle 40, through which gas can be injected into the first mold cavity 20, FIGS. 1-4. One of the mold parts (the first mold part 11 in FIG. 1) can be configured to have a recess, or aperture 50 for receiving a relatively small amount 15a of the first plastic material 15 during the injection process. A solidified portion of this relatively small amount 15a of the first plastic material 15 will form a flap 60 when molding and solidification of the first plastic material 15 is complete. For this reason, the recess, or aperture 50 will be termed herein as "flap aperture."

Figure 2:
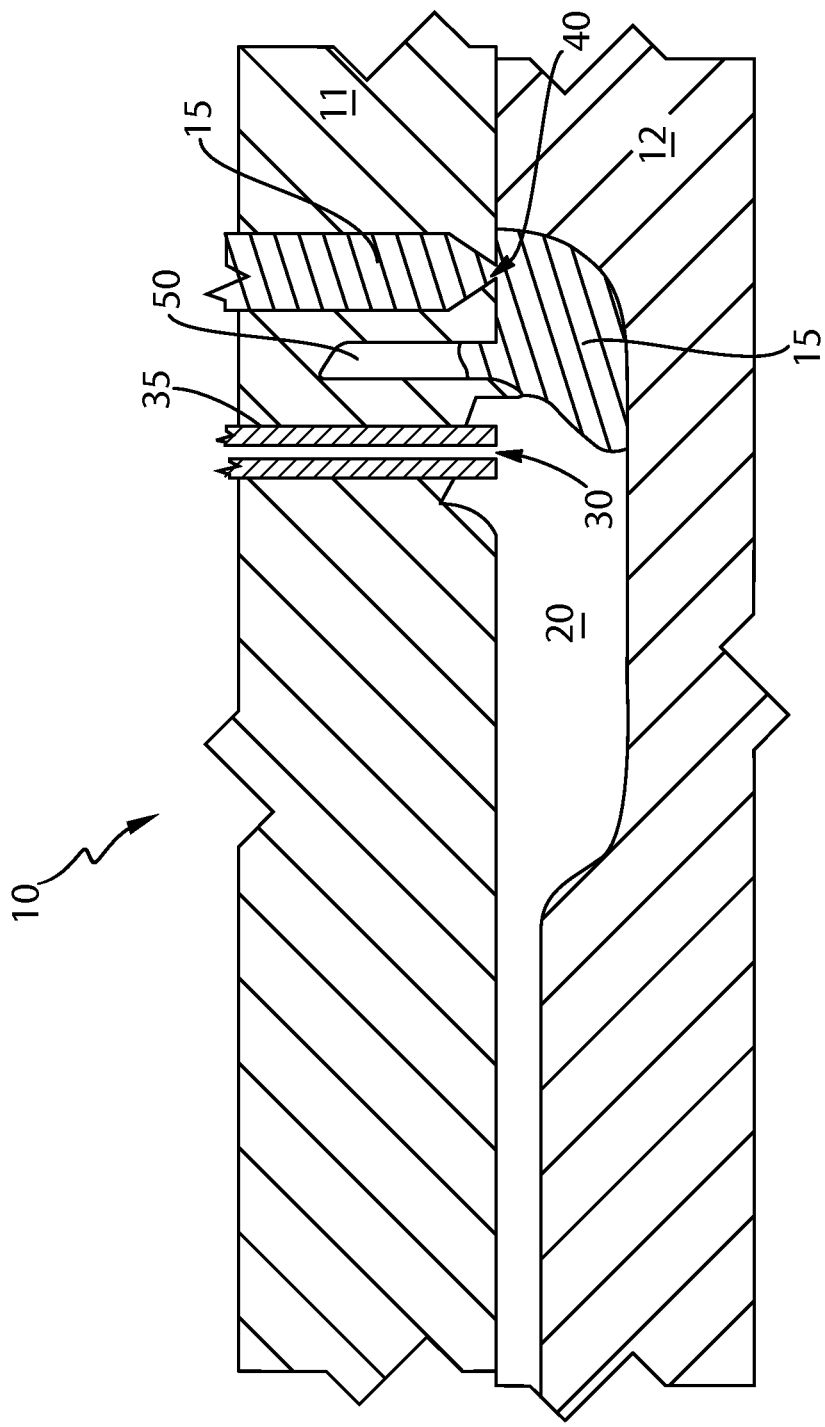
FIG. 2 schematically shows a partial cross-sectional view of the first mold bar shown in FIG. 1 and illustrates an initial phase of the injection-molding process.
Figure 3:
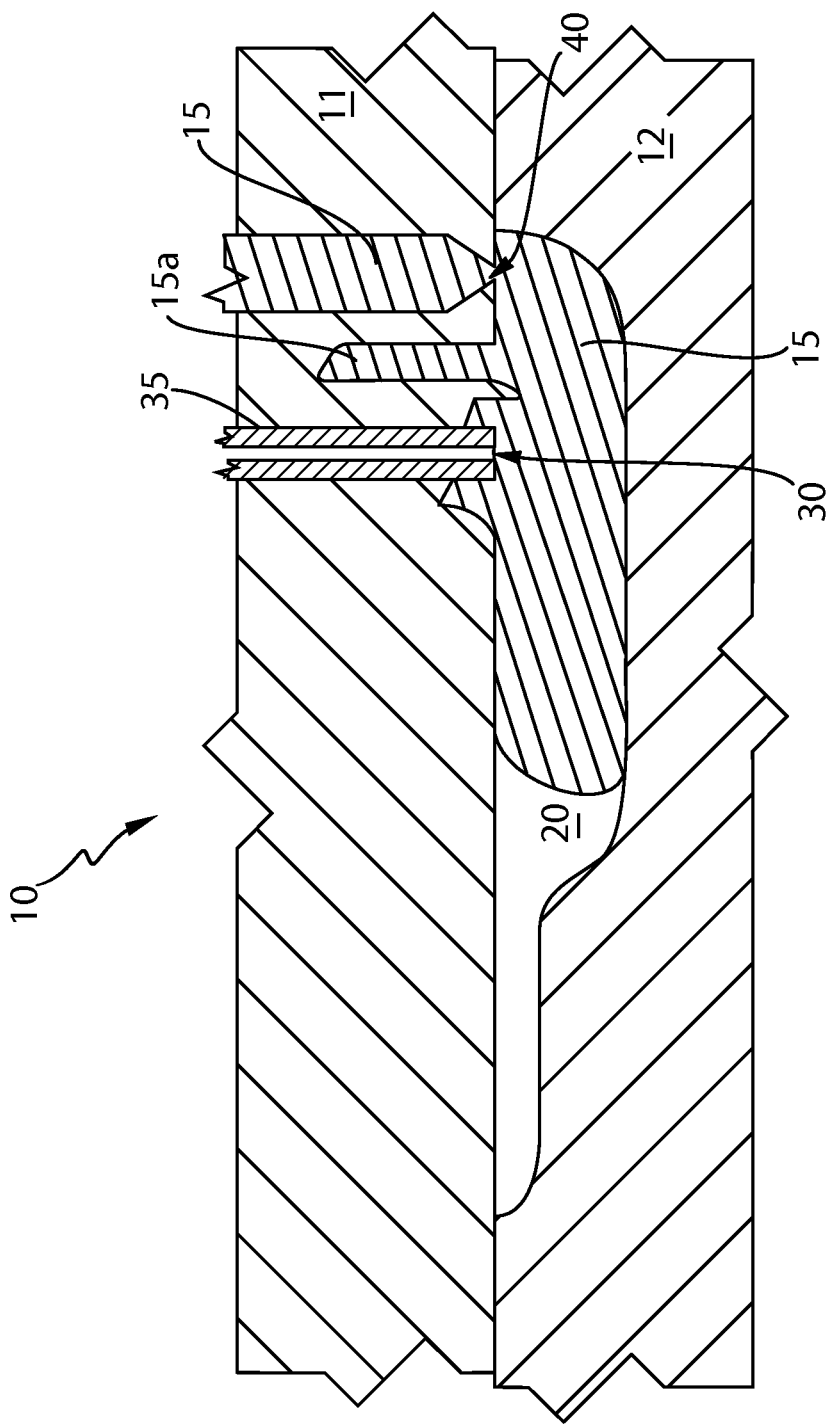
FIG. 3 schematically shows a partial cross-sectional view of the first mold bar shown in FIGS. 1 and 2 and illustrates advancement of a first molten material inside a first mold cavity.
Figure 4:
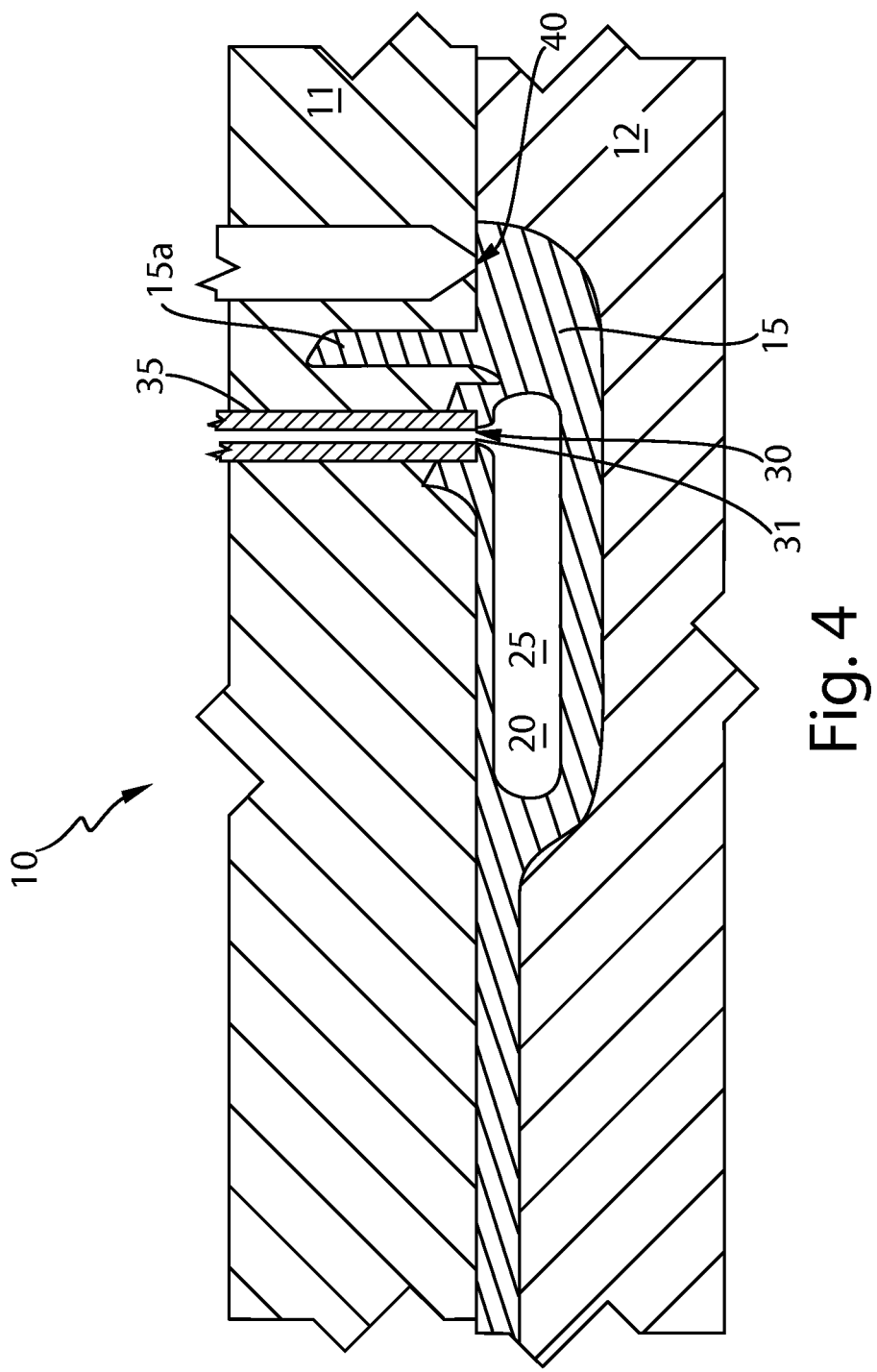
FIG. 4 schematically shows a partial cross-sectional view of the first mold bar shown in FIGS. 1, 2, and 3 and illustrates the process when the first mold cavity is filled with the first molten material.
Figure 5:
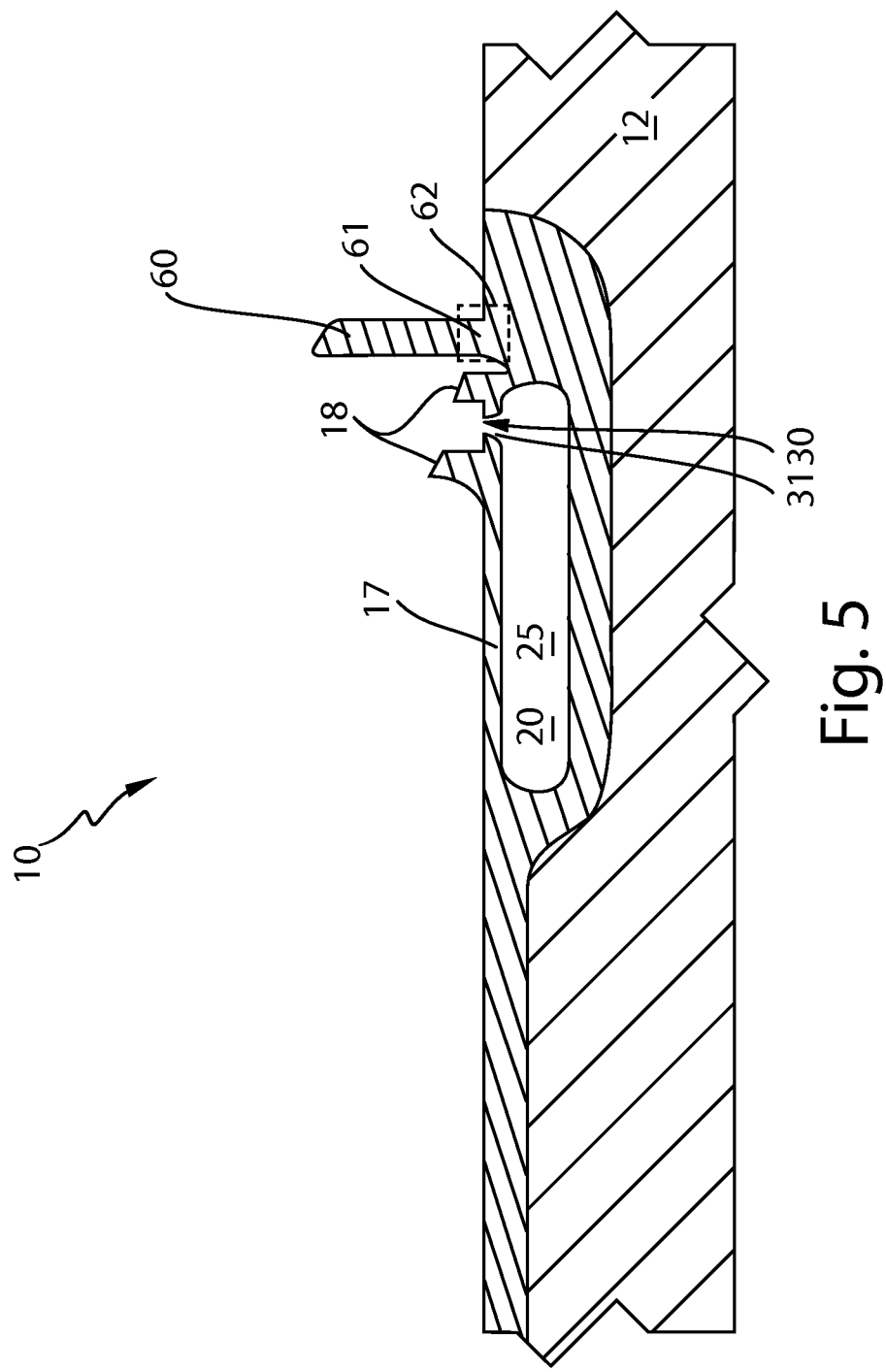
FIG. 5 schematically shows a cross-sectional view of a hollow body comprising a first plastic material, including the flap.

FIGS. 2 and 3 show progression of the first plastic material 15, injected into the first mold cavity 20 from the plastic-injection nozzle 40, inside the cavity 20. While advancing inside the cavity 20, the first plastic material 15 fills the flap recess 50, FIG. 3. When the first mold cavity 20 is sufficiently filled, i.e., when it is from about 50% to about 95% full, the injection of the first plastic material 15 is suspended, using, e.g., a valve-gate mechanism or any other suitable flow-checking mechanism known in the art. Additionally, embodiments of a gas-assisted injection molding are known wherein gas is injected with some portion of the first plastic material. An advanced pressure control algorithm can be used to ensure that plastic pressure at the plastic injection nozzle exceeds gas injection pressure at the gas nozzle, thus preventing reverse flow of the plastic material in the plastic injection nozzle.

Following the suspension of injection of the first plastic material, a fluid, such as an inert gas, can be injected into the first mold cavity 20—and thus into the molten first plastic material—though the fluid-injection nozzle 30. The injected gas, expanding in the cavity 20 under pressure, forms a void 25 in the first molten plastic material 15, FIG. 4. The pressurized injected gas also causes the first molten plastic material 15 to substantially conform to the geometry of the mold cavity's walls. After at least a portion of the first plastic material 15 solidifies, the gas contained within the void 25 can be allowed to escape through an opening, or vent 31 created in the at least partially solidified first material 15 by the movement of the gas.

After the gas is vented out, the pressure inside the void 25 becomes approximately equal to the atmospheric pressure. The first and second mold parts 11, 12 can now be disengaged, and a solidified first body 17, comprising the first plastic material 15, can be removed from the first mold for further processing. Alternatively, the solidified first body 17 can continue to be disposed in one of the mold parts (the second mold part 12 in FIG. 5). Said one of the mold parts (the second mold part 12 in FIG. 5) can thus become a part of a subsequent, second mold bar, in which the solidified first body 17 will be overmolded by a second plastic material.

Figure 6:
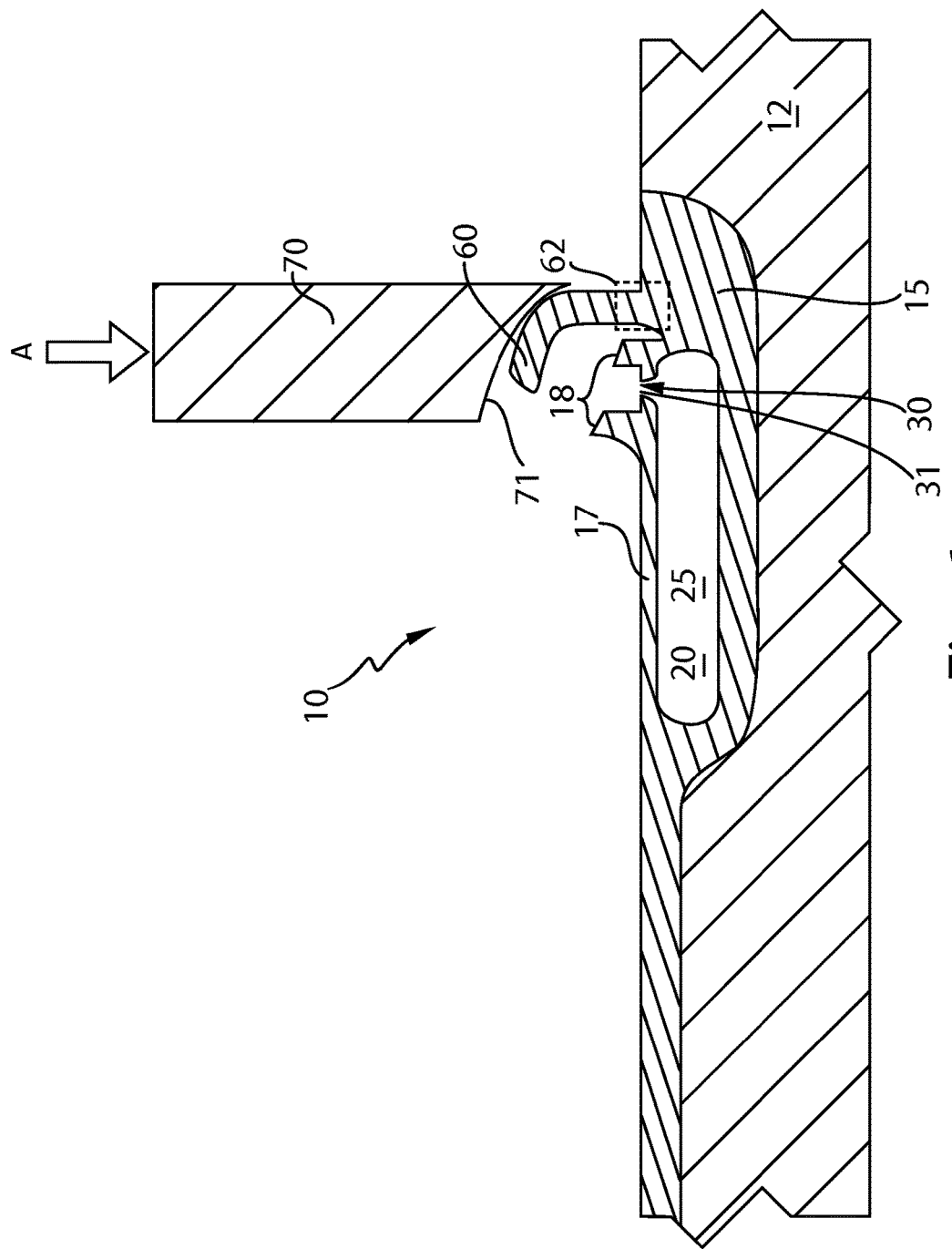
FIG. 6 schematically shows a cross-sectional view of the hollow body shown in FIG. 5 and a closing tool engaging the flap.
Figure 7:
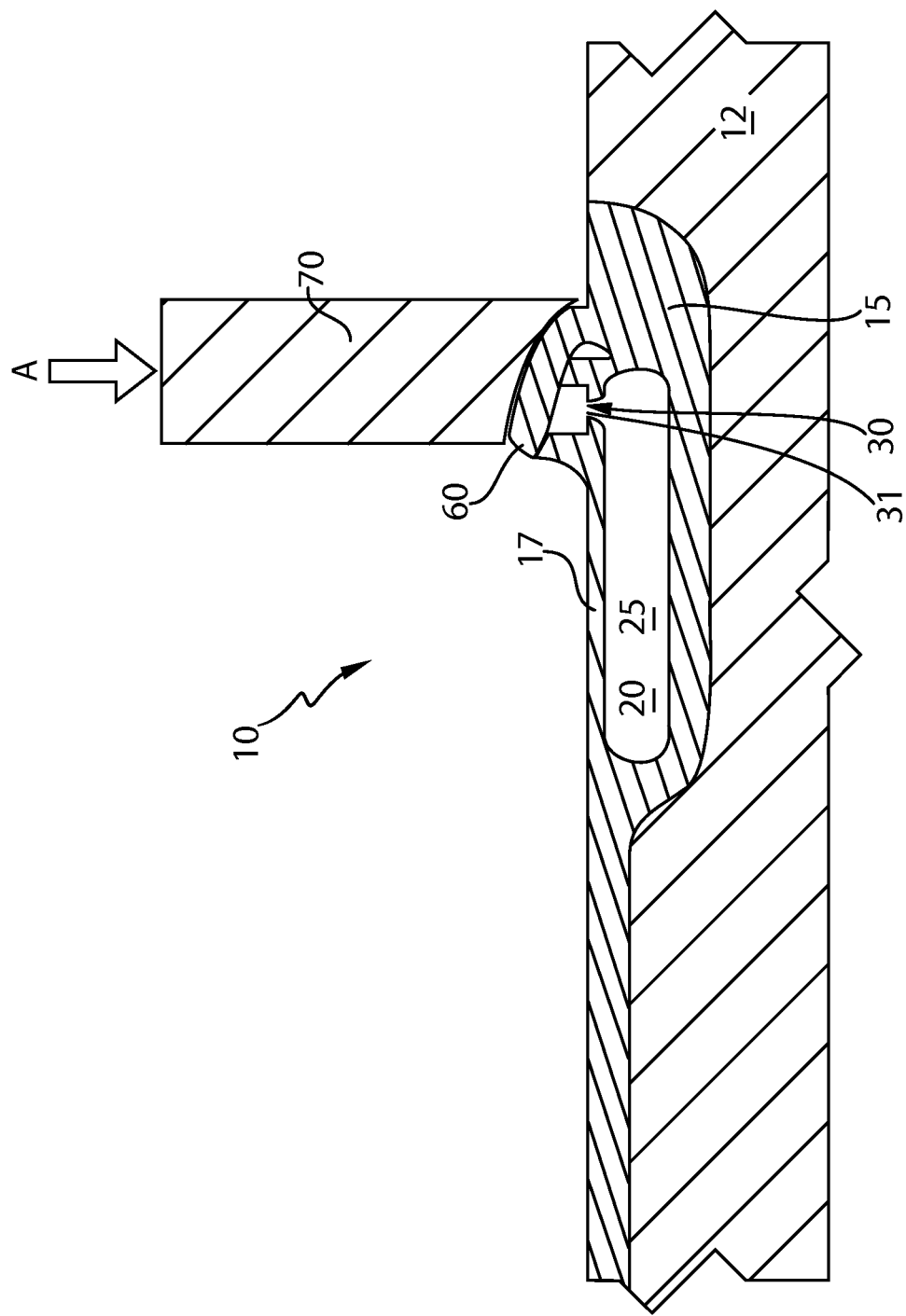
FIG. 7 schematically shows a cross-sectional view of the hollow body shown in FIGS. 5 and 6, wherein the closing tool has substantially bent the flap over the vent extending through a wall of the hollow body.
Figure 8:
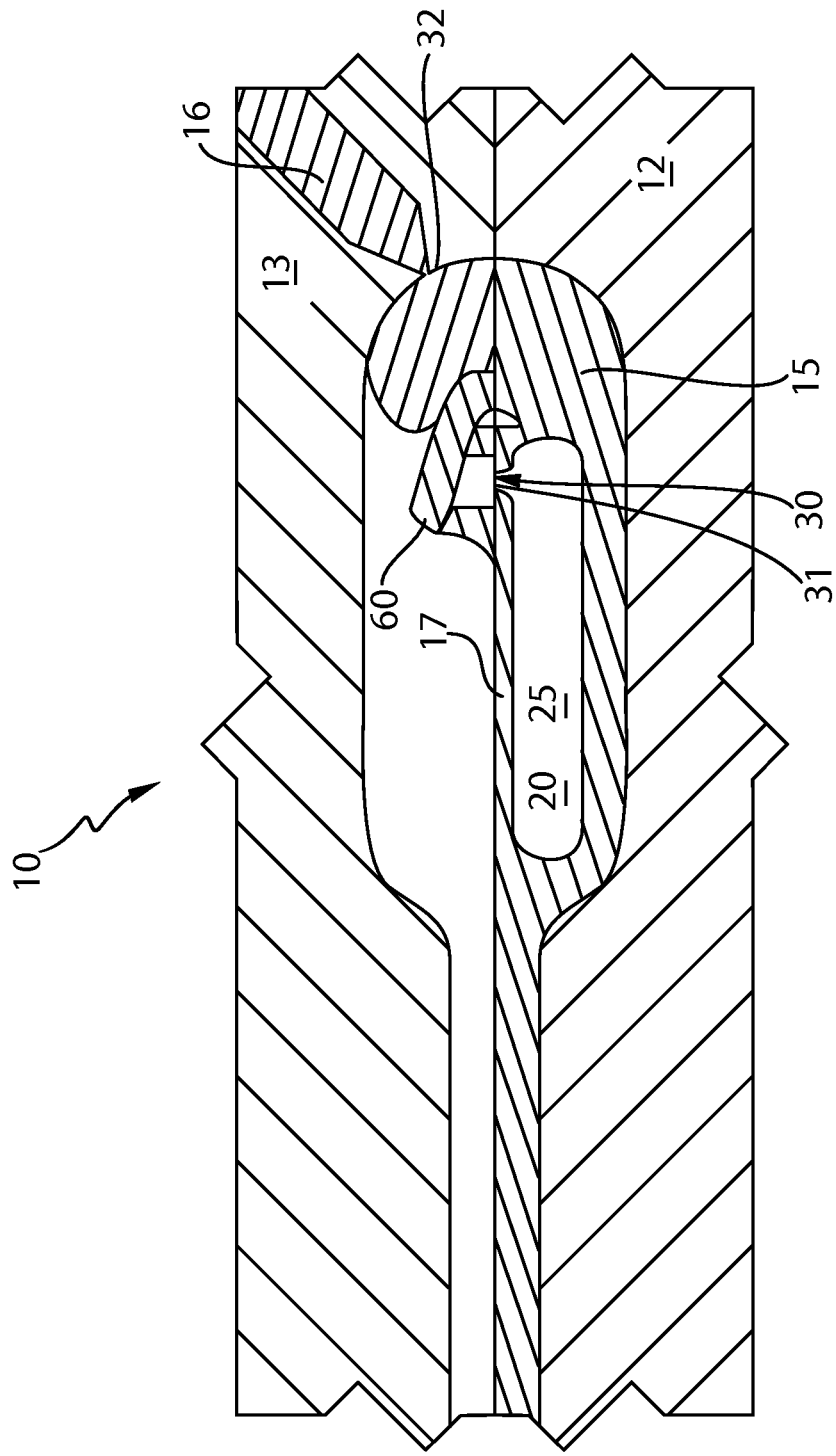
FIG. 8 schematically shows a partial cross-sectional view of an embodiment of a second mold bar having the hollow body therein, the hollow body having the flap closing the vent, and illustrates an embodiment of an injection-molding process when a second material is injected into a second mold cavity to at least partially cover the closed flap.

The hollow first body 17 has the vent 31 extending through body's wall into the void 25 and a flap element 60. The flap 60, formed from a portion of the first material 15a (FIG. 3), is located in sufficient proximity to the vent 31. The flap 60 is a flexible element made from the first plastic material 15 and comprising a living hinge 61, FIG. 5. The living hinge 61 is structured and configured to allow the flap 60 to articulate (through bending, folding, and the like movements) between a first, unfolded position (FIG. 5) and a second, folded position (FIG. 7). When the flap 60 is in the first position, the vent 31 is open. When the flap 60 is in the second position, the flap 60 sufficiently covers the vent 31, obstructing passage of a fluid into the hollow first body 17 through the vent 31. This will substantially prevent a subsequent molten material from entering into the void 25 through the vent 31. The living hinge 61 may beneficially include a designated strain zone 62 (FIGS. 5, 6), where the bulk of the strain necessary to allow the flap 60 to articulate from the first position to the second position is being primarily distributed.

Figure 18:
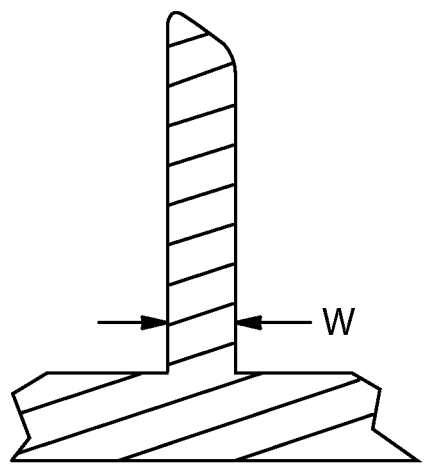
FIGS. 18 and 19 schematically show partial cross-sectional views of an embodiment of a flap in an unbent position (FIG. 18) and in a partially bent position (FIG. 19).
Figure 19:
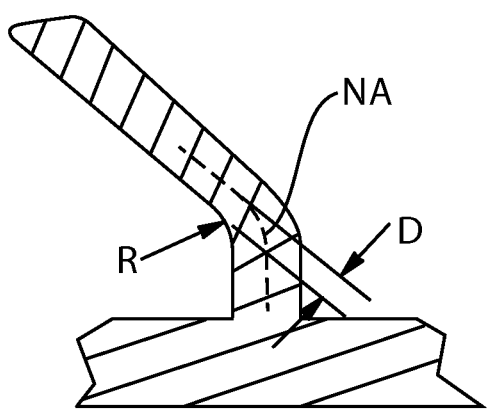

There is a variety of materials that can be used to form the flap 60—and a number of geometries to design the functional living hinge 61. One way of approaching this task is to treat the flap as an Euler-Bernoulli beam, FIGS. 18 and 19. Then, when the flap 60 folds or bends, the strain in the flap 60 reaches its maximum $S_{max}$ at the surfaces of the flap in the bending zone. This maximum strain $S_{max}$ at this surface of the flap 60 in the bending zone can be approximated as: $S_{max}=D/R$, where "D" is the distance between the surface of the flap 60 and its neutral axis NA, and "R" is the bend radius (FIG. 19). A further approximation for rectangular cross sections is that the neutral axis NA is close to the centerline of the beam such that $S_{max}=W/2R$, where "W" is a thickness of the flap 60 in the bending zone.

As is well known, every material has a maximum allowable strain, $S_{limit}$, beyond which the material will fracture.

Thus, for the flap 60 to bend to the required limit without the risk of fracture, both material constraints and geometric constraints can be taken into account. With respect to the former, the flap 60 should be sufficiently ductile; and with respect to the latter, the flap 60 should be sufficiently thin, to bend to the required bend radius R. Generally, the flap 60 can satisfy the following formula: $W/2R<S_{limit}$. In some embodiment, the flap 60 can beneficially satisfy the following formula: $W/R<S_{limit}$.

One exemplary, non-limiting, material that can satisfy the above formula is polypropylene. For example, the flap 60 made of polypropylene and having a thickness of 0.5 mm and a hypothetical limit strain of 65% ($S_{limit}$=0.65 mm/mm), to be able to bend without fracture, can have the bend radius according to the following formula: (0.5 mm)/2R<0.65. To state this differently, the bend radius R, as measured with respect to the inner surface of the flap 60 (FIG. 19), can be 0.38 mm or greater. Such a small bend radius implies that the material may be bent nearly double (a so-called "hairpin" bend) at low risk of fracture. Other materials, e.g., such as acrylonitrile butadiene styrene plastic (ABS), having a limit strain of about 20% would require a larger bend radius, or a thinner wall, or both, to create the flap 60 while minimizing or avoiding the risk of fracture.

As one skilled in the art will recognize, material properties can vary from lot to lot; and thus it may be advisable to incorporate a safety factor in these considerations, especially when millions of articles per year are manufactured and statistical variations of a number of standard deviations from normal must be taken into account. Therefore, the flap 60 made of a polypropylene can beneficially have an inner bend radius R of at least 1 mm, at least 2 mm, or at least 3 mm. Further, the flap 60 does not need to form a completely hermetic, air-tight seal around the vent 31. As long as the second (or any subsequent) plastic material, which overmolds the solidified follow body 17, including the flap 60, does not significantly penetrate through the vent 31, the flap 60 performs its intended function. Therefore, the inner bend radius R can be greater than indicated herein above, depending on the viscosity of the plastic material overmolding the flap 60 and the vent 31 and the geometry of the relevant portions of the flap 60 and the vent 31.

A closing tool 70 (FIGS. 6, 7, 12-17) can be used to cause the flap 60 to articulate about its living hinge 61 towards the vent 31. The flap 60 can be bent or folded by the closing tool 70 so that the strain in the living hinge 61, induced by the bending or folding, is primarily distributed in the designated strain zone 62. The closing tool 70 can comprise any suitable device structured and configured to cause the flap 60 to securely cover the vent 31. The closing tool 70 may comprise a pin, a beam, a bar, an injection-molded insert or other feature, a welding horn, a machined or milled structure, or a turned structure (i.e., one manufactured on a lathe). The closing tool can be stationary or movable. In an exemplary embodiment of FIGS. 6 and 7, the closing tool 70 comprises a mechanical pin structured to move relative to the flap 60. The pin 70 has a working surface 71, configured to contact the surface of the flap 60 and to direct the bending or folding of the flap 60 in the desired direction as the pin 70 moves relative to the flap 60. In an exemplary embodiment of FIGS. 6 and 7, the pin 70 is structured to travel in the direction of an arrow A. The pin's working surface 71 can have an inclined concave portion, forcing the flap 60 to smoothly glide along the working surface 71 as the pin 70 advances in the direction of the arrow A. Once the flap 60 is fully folded over the vent 31, the pin 70 stops its movement in the direction of the arrow A, FIG. 7.

The living hinge 61, including its designated strain zone 62, is designed to ensure that the flap 60 neither folds/bends sideways nor breaks off from the rest of the first plastic body 17 during the flap's folding or bending. To facilitate a more precise bending or folding of the flap 60, the working surface 71 of the tool 70 and a corresponding portion of the surface of the flap 60 to be contacted by the working surface 71, may comprise mutually engageable guide elements, such as, i.e., mating grooves/channels and projections/ridges, the latter configured to glide inside the former. These embodiments are not illustrated herein—but can be easily visualized by one skilled in the art.

Likewise, the first plastic body 17, including the flap 60, can be beneficially constructed to include surface features that would couple with, or engage, a corresponding surface of the flap 60 to facilitate the closure of the vent 31 with the flap 60. Such features may include, e.g., crush ribs, ridges, textured surfaces, sharp points, fins, channels, grooves, and other mating structures known in the art. In the exemplary embodiment of FIG. 5-7, a portion of the first plastic body 17's surface immediately surrounding the vent 31 includes a flap-contacting surface 18 comprising protrusions. The flap-contacting surface 18 can be configured to at least partially mate with a corresponding surface of the flap 60, when the flap 60 is fully bent or folded.

Additionally or alternatively, the flap 60 can be molded to include features facilitating the mating of the flap 60 with the flap-contacting surface 18 to ensure secure closure of the vent 31. An embodiment is contemplated in which both the flap-contacting surface 18 and the flap 60 include mating features structured and configured to lock the flap 60 in the second, closed position. Although the several drawings herein schematically show the flap 60 as overlapping the vent 31 (FIG. 7), it should be appreciated that the first plastic article 17, including its flap-contacting surface 18, and the flap 60 may be designed so that the flap 60 is flush with the article's surface immediately surrounding the closed flap 60 when the flap 60 is in the second position.

While the figures herein show the working surface 71 having a generally concave shape, the invention is not limited to such or similar configurations. The working surface 71 may comprise any suitable shape, such as, e.g., an inclined planar shape, convex shape, or any combination of flat/planar and curved surfaces. Nor is the invention limited with respect to the direction of the movement of the closing tool 70. An embodiment of the process in which the tool 70 moves, e.g., in a direction perpendicular to the direction of arrow A, e.g., from right to left in FIG. 6, can be readily visualized by one skilled in the art. In such a case, the tool 70 will, of course, have the working surface different from the one shown in the figures herein. Likewise, the tool 70 can be configured to have a multi-directional, complex movement, e.g., a combination of the movement in the direction of the arrow A and the movement in the direction perpendicular to the arrow A (not shown). Lastly, one skilled in the art will readily recognize that the movement of the tool 70 towards the flap 60, described herein with reference to FIGS. 6 and 7, is to be understood as a relative movement; in other words, the invention contemplates embodiments in which the first plastic body 17 moves relative to the tool 70 that is stationary, as well as an embodiment in which both the tool 70 and the first plastic body move relative to one another. All of these embodiments, together with the embodiments illustrated herein, are within the scope of the invention.

After the flap 60 is moved into the second position, in which the flap 60 covers the vent 31, the flap 60 can be bonded, permanently or temporarily, to the underlying or surrounding structure, e.g., the hollow article's surface surrounding the vent 31. The permanent bonding can be accomplished by using any known means, such as, e.g., sonic or ultrasonic welding. In this instance, closing tool 70 can comprise a weld horn. Other means of bonding the flap 60, in the second position, and the vent-surrounding area include, without limitation, gluing, friction, undercut or latch fits (snap fits), heat staking, re-melting, chemical bonding, or solvent welding. Alternately, the flap may be held loosely in place, e.g., by the closing tool 70, as is described herein below with respect to several exemplary embodiments.

In a following step, a second mold bar, having a second mold cavity 22, can be formed. In an exemplary embodiment of FIG. 8, the second mold cavity 22 is formed between the second mold part 12 and a third mold part 13. A second plastic material 16 can be injected into the second mold cavity 22 to at least partially overmold the first hollow body 17 disposed therein, including the flap 60 being in the second, closed position. A second-plastic injection nozzle 32, through which the second plastic material is injected, can beneficially be located in relative proximity to the closed flap 60—and particularly in close proximity to the flap's hinge 61, so that the second plastic material 16 can secure the hinge 61 in the folded position. Securing the flap 60 in the closed position over the vent 31 prevents the second material 16 from penetrating, through the vent 31, into the void of the first hollow body 17.

Additionally or alternatively, the movement of the second plastic material 16 inside the second mold cavity 22 can cause, or at least facilitate, the closing of the flap 60. This can be done if the flap's hinge 61—or the flap 60 as a whole—is designed to articulate, fold, or bent in a direction of closing the flap 60 under the pressure exerted by the moving second plastic material 16, pushing the flap 60 in the direction of the closing (e.g., from right to left in FIG. 8), thereby folding or bending the flap 60 into the second position over the vent 31.

Figure 9:
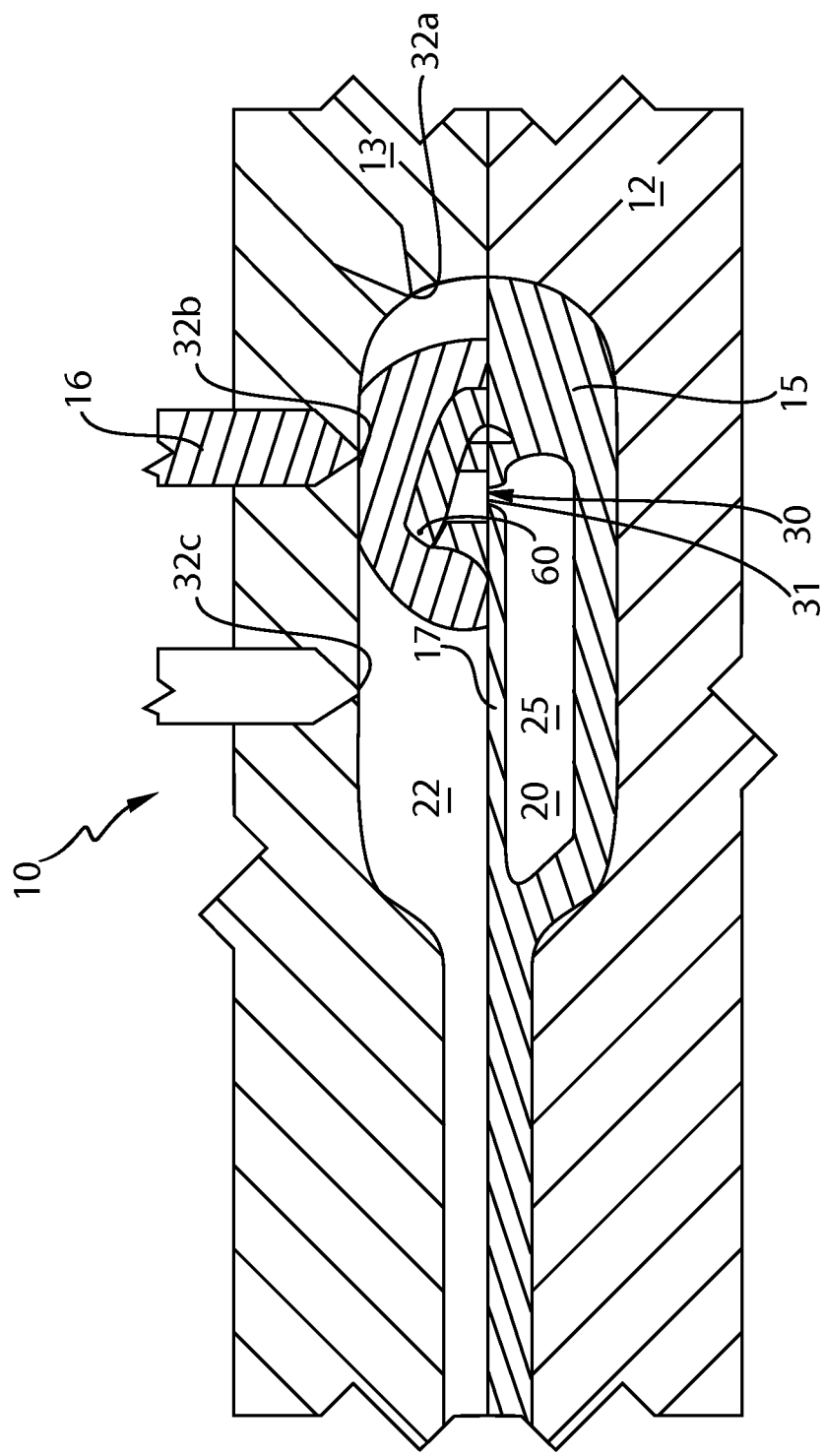
FIG. 9 schematically shows a partial cross-sectional view of another embodiment of the second mold bar having the hollow body therein, the hollow body having the flap closing the vent, and illustrates another embodiment of the injection-molding process when the second material is injected into the second mold cavity to at least partially cover the closed flap.
Figure 10:
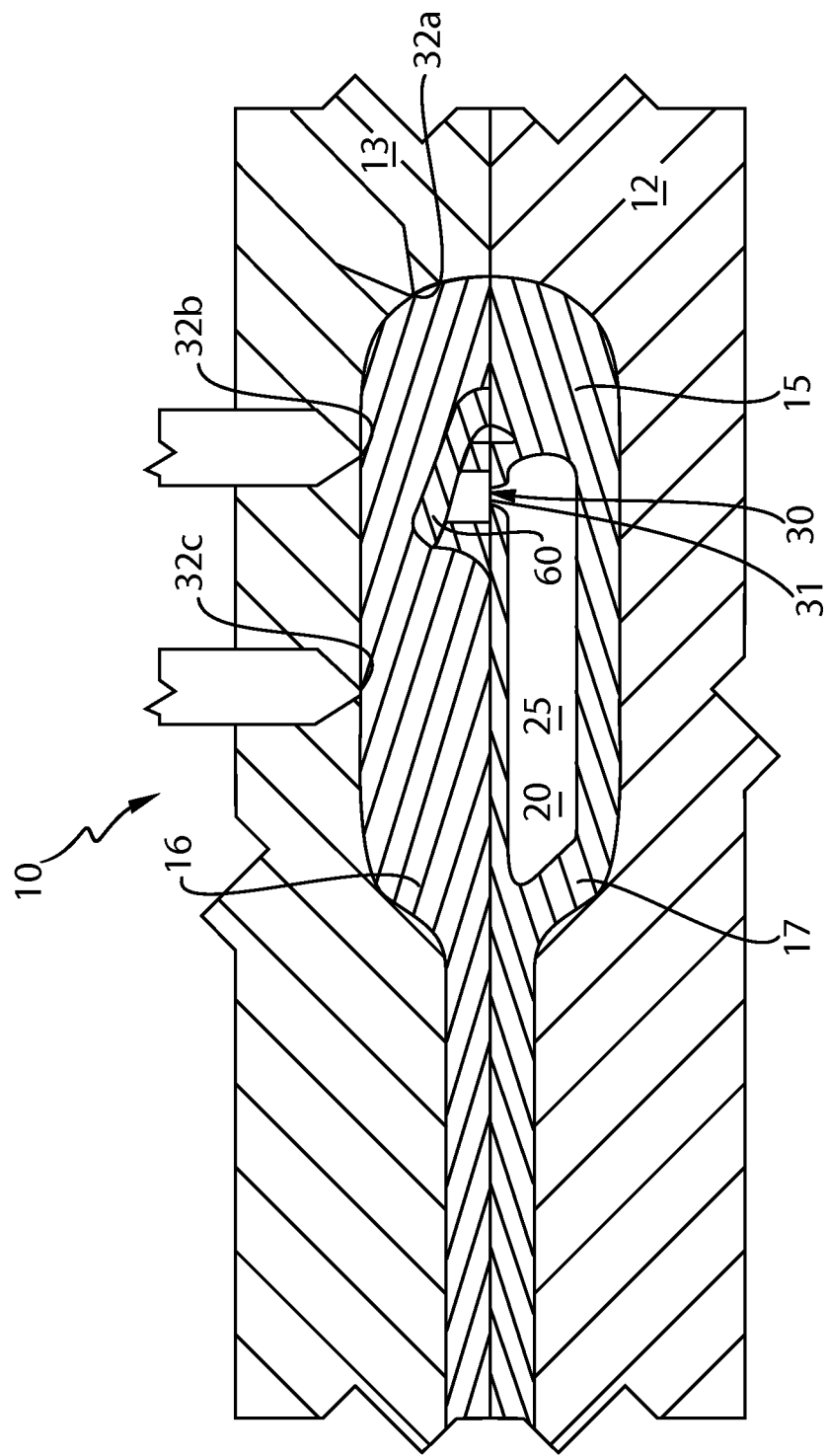
FIG. 10 schematically shows a partial cross-sectional view of yet another embodiment of the second mold bar having the hollow body therein, the hollow body having the flap closing the vent, and illustrates yet another embodiment of the injection-molding process when the second material is injected into the second mold cavity to at least partially cover the closed flap.
Figure 11:
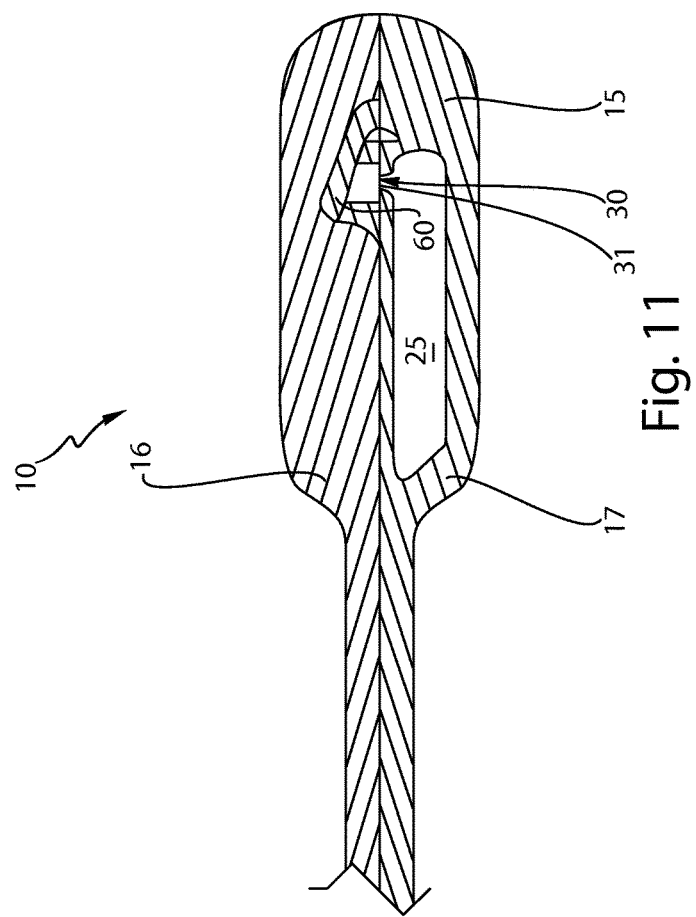
FIG. 11 schematically shows a finished multi-component article comprising the hollow body made of the first plastic material being at least partially overmolded with the second plastic material.

In an exemplary embodiment of FIG. 9, there are three second-plastic injection nozzles in the mold: 32a, 32b, and 32c. In this embodiment, the process of injection can be structured to begin with the injection of the second material 16 through the injection nozzle 32b closest to the folded flap 16. After the flap 60 is sufficiently secured in place, the second material can be injected through all the three second-material injection nozzles 32a, 32b, 32c, to have the hollow body 17 at least partially overmolded with the second material 16, FIGS. 10 and 11.

Figure 12:
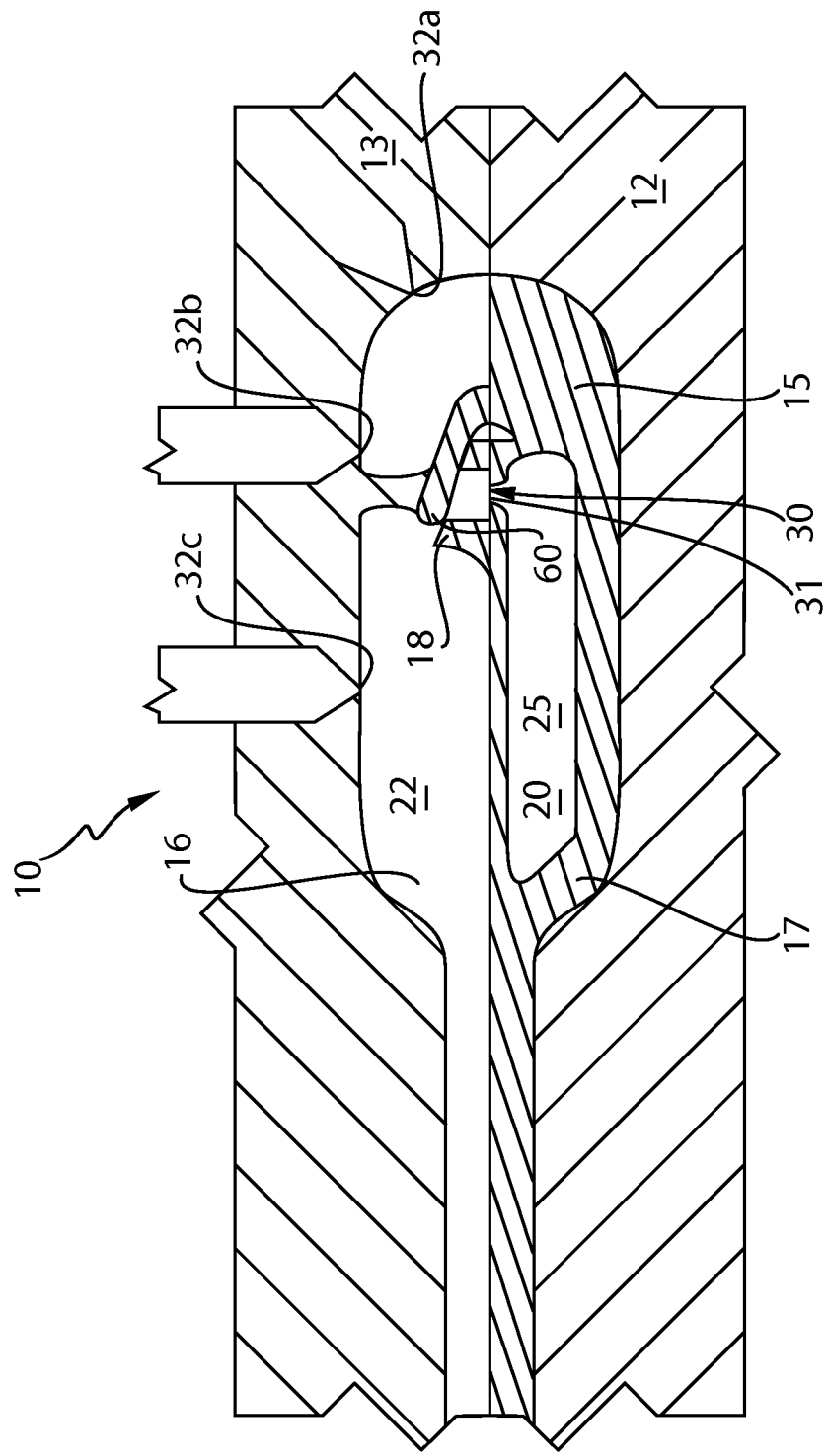
FIG. 12 schematically shows a partial cross-sectional view of an embodiment of a second mold bar having a hollow article disposed therein, the hollow article having a vent and a movable flap, the second mold comprising a closing tool structured and configured to move the flap into a closed position, in which the flap overlaps the vent.
Figure 13:
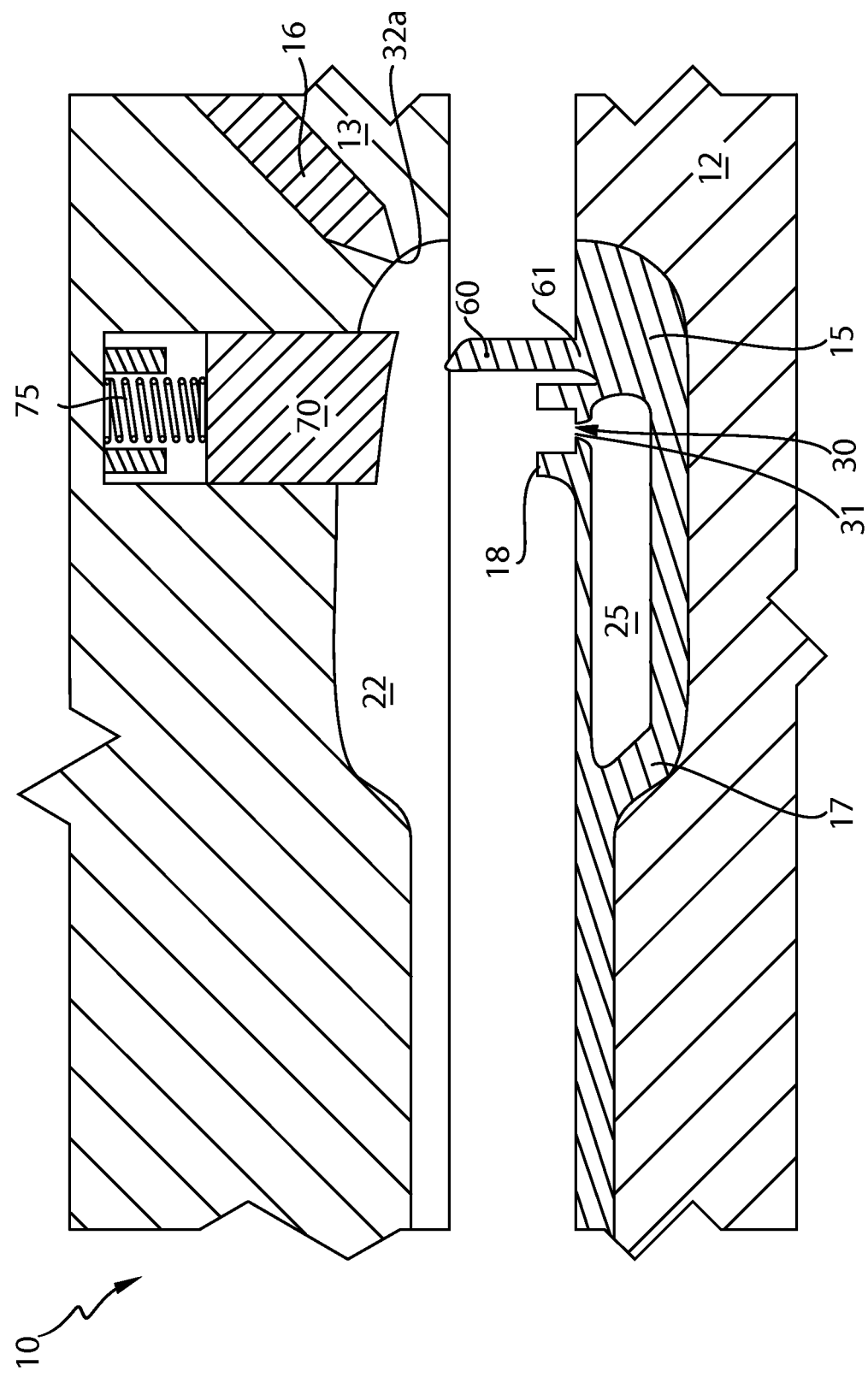
FIGS. 13-17 schematically shows partial cross-sectional views of an embodiment of a second mold bar having a hollow article disposed therein, the hollow article having a vent and a movable flap, the second mold comprising with a closing tool structured and configured to move inside the mold to contact the flap and to move the flap into a closed position, in which the flap overlaps the vent.
Figure 14:
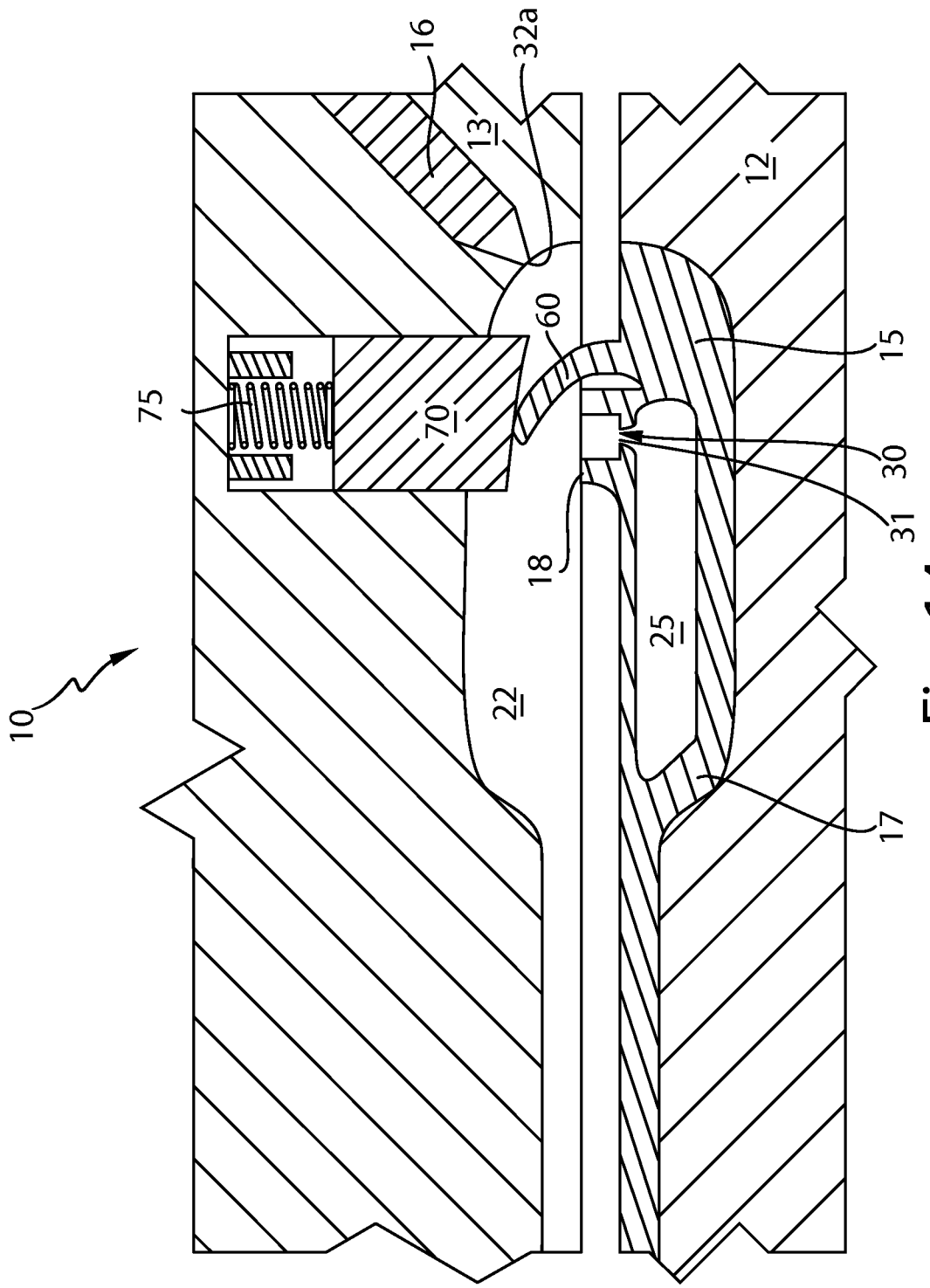

In an exemplary embodiment of FIG. 12, the third molding part 13 comprises the closing tool 70. When the molding parts 12, 13 engage one another, thereby forming the second mold cavity 22 having therein the hollow body 17, including the flap 60 in the first position, the closing tool 70 compresses the flap 60 in a manner similar to that described herein above. If the closing tool 70 in this embodiment stays in contact with the flap 60 during the injection of the second material 16, a portion of the flap 60 can be left exposed, i.e., not covered by the second material 16. Unless it is desired to leave this portion exposed in the final product, it may be beneficial to overmold the flap's exposed portion with a third material in a subsequent molding step. But in all instances, the void 25 inside the hollow body 17 is still sufficiently sealed during the second molding step and for the intended useful duration of the multi-component molded article.

Figure 15:
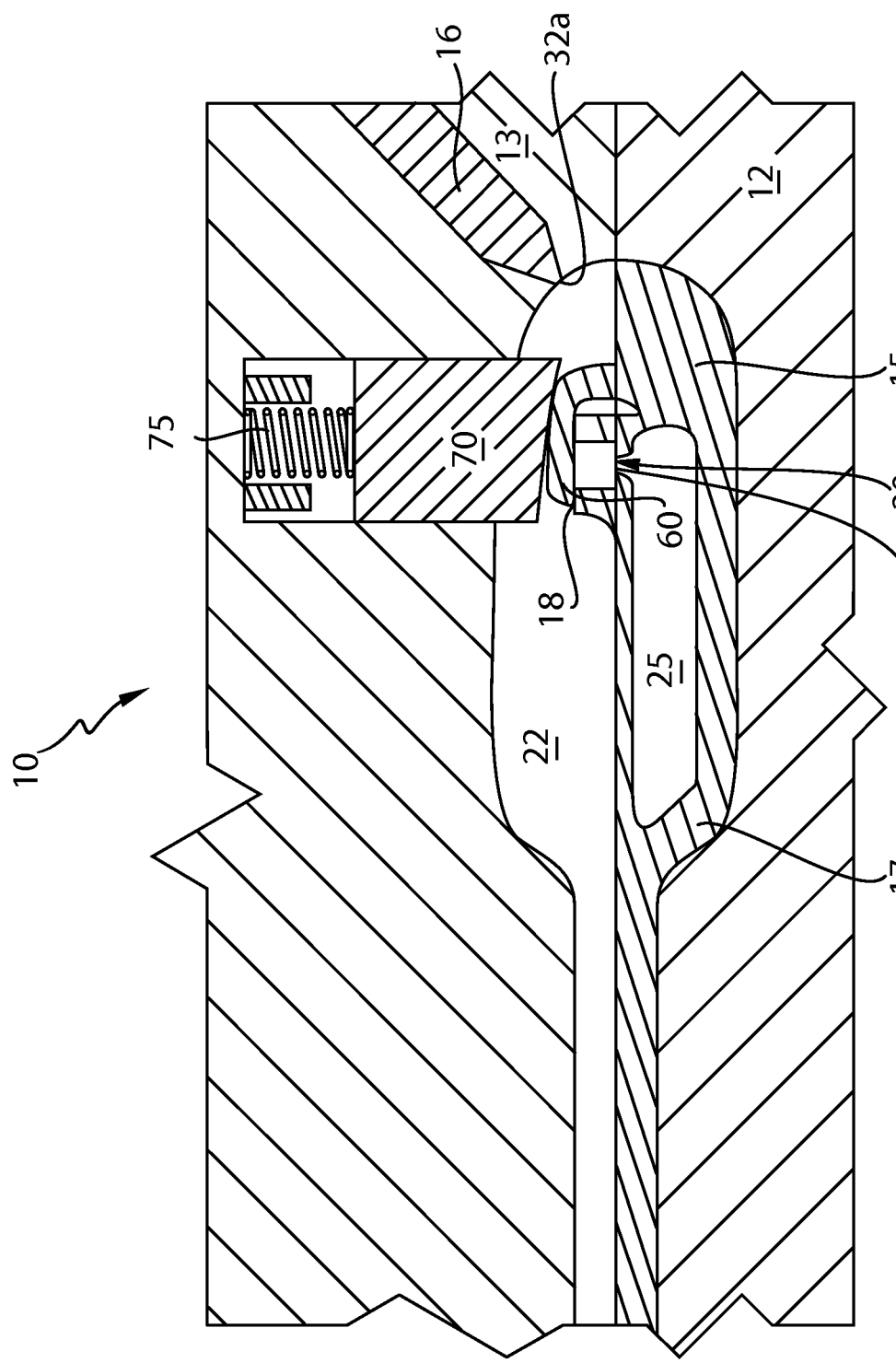
Figure 16:
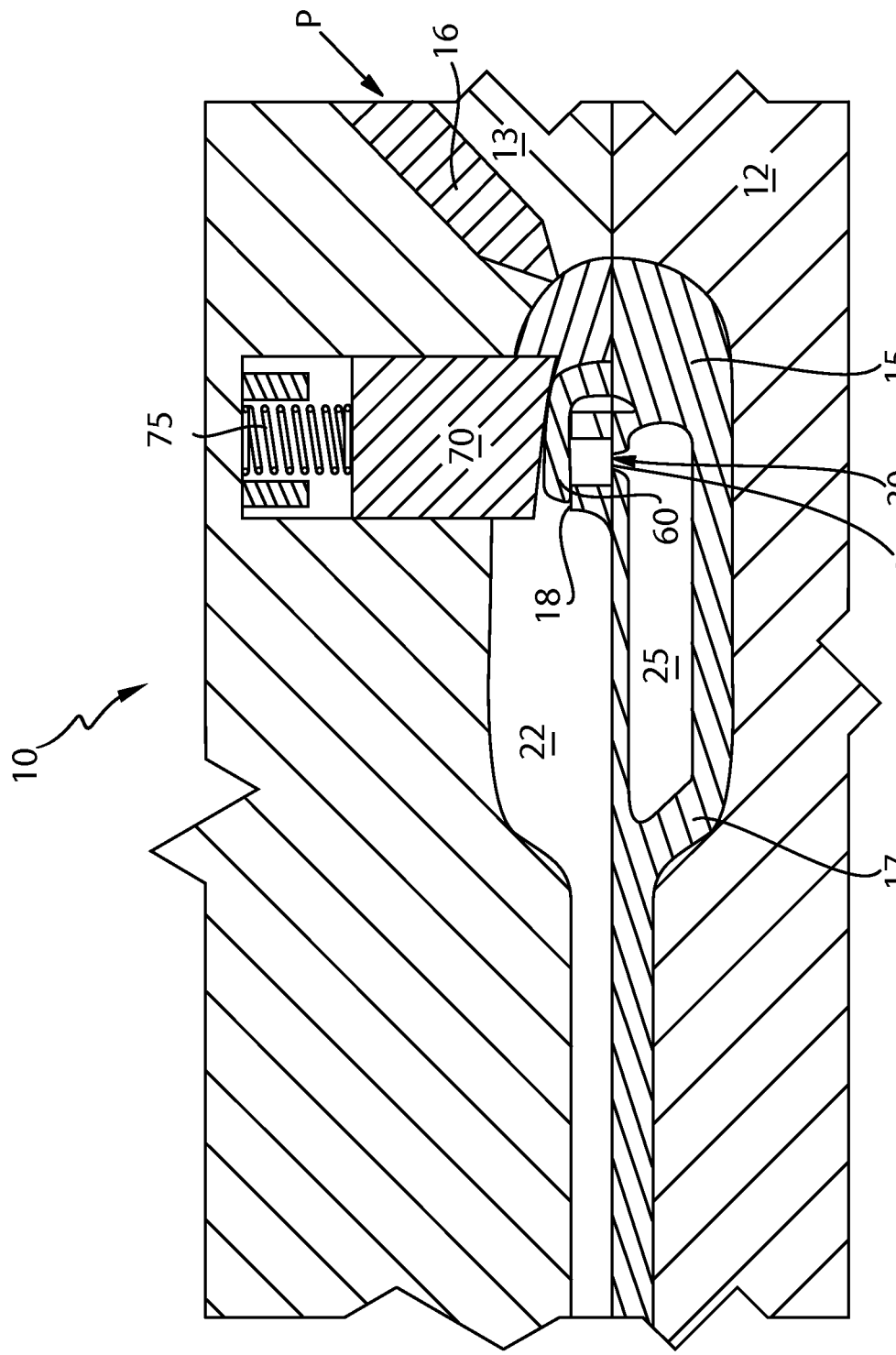
Figure 17:
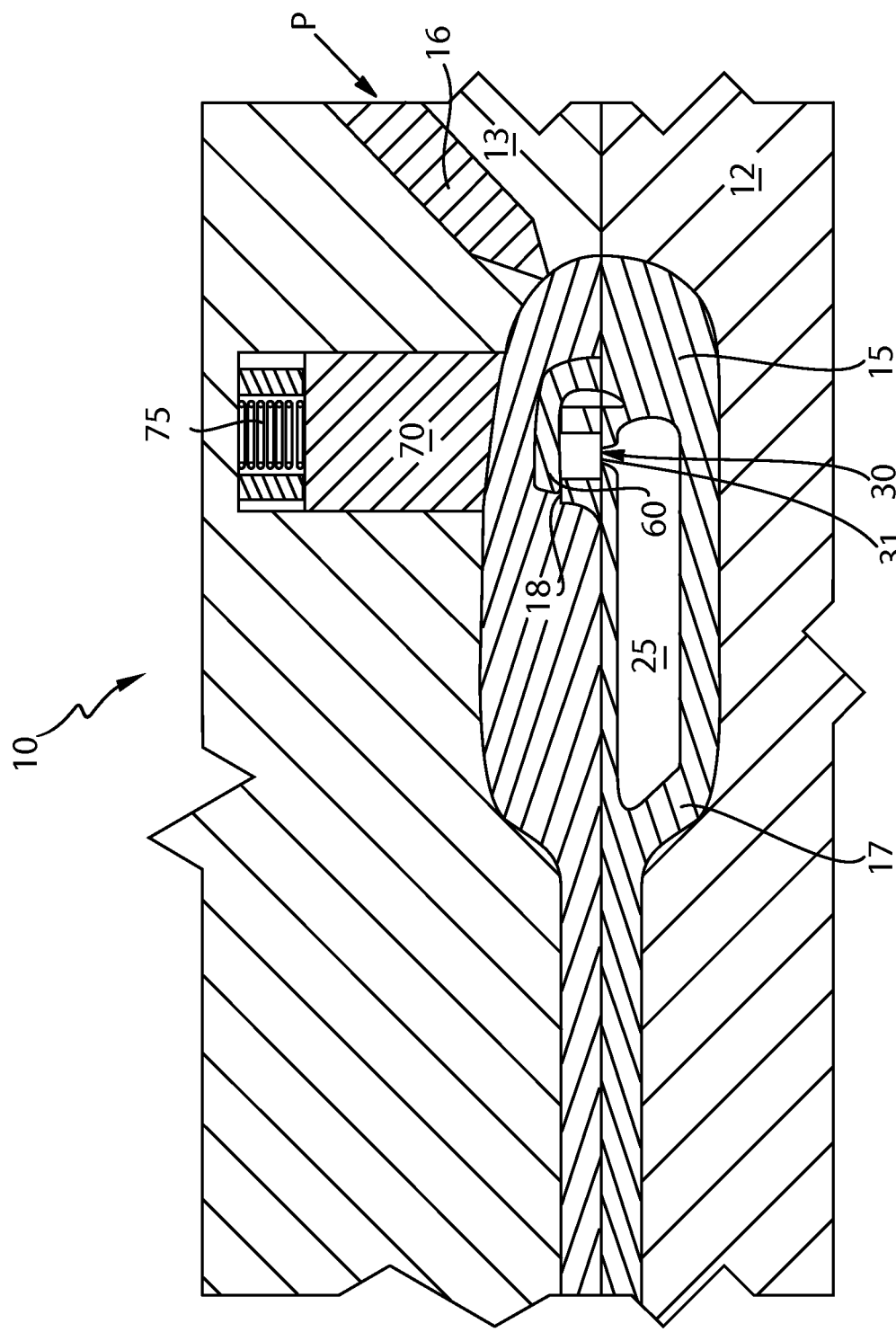

In an exemplary embodiment of FIGS. 13-17, the closing tool 70 is shown as a pin structured and configured to move inside the mold. In this embodiment, the closing tool 70 is configured to slide inside one of the mold parts to extend therefrom into the second mold cavity 22 (FIGS. 13-16) and to withdraw into the mold to form a part of the surface of the mold cavity 22 (FIG. 17). The pin 70 can be held in an extended position by any suitable finite force, e.g., a spring 75 or hydraulic pressure (not shown), which can be partially overcome by the pressure resulting from the contact between the pin 70 and the flap 60 (FIGS. 14, 15) when the second and third mold parts 12, 13 move towards one another to form a second mold cavity 22 therebetween. FIG. 15 illustrates the fully formed second mold cavity 22 with the pin 70 extending into the second mold cavity 22 and holding the flap 60 in the closed position. In FIG. 16, the second plastic material 16 is shown as being injected into the second mold cavity 22, exerting a pressure on the pin 70, which causes the pin 70 to gradually move into the mold. Eventually, the pressure differential between the molding pressure of the second material 16 and the pressure exerted by the pin 70 forces the pin 70 to fully retract into the mold (FIG. 17). The pin's working surface 71 can be configured to form part of the molding cavity's surface when the pin is fully recessed inside the mold.

Injection of the second plastic material 16 is complete when the second mold cavity 22 is substantially filled with the second plastic material 16. Following sufficient solidification and cooling of the second material 16, a multi-component article, comprising the hollow body 17 at least partially overmolded by the second plastic material 16, can be ejected from the second mold cavity 22. Because the closed flap 60 has prevented the second plastic material 16 from penetration into the hollow body 17 through the vent 31, the finished article is substantially free from the second material 16 being disposed inside the hollow body 17.

In a further embodiment of the process, a portion of the second plastic material 16 can be injected at a substantially low constant pressure, so that the sealed void 25 inside the hollow body 17, formed during the sealing of the vent 31, is not substantially decreased in volume during the injection of the second plastic material 16. In such an embodiment, the void 25 inside the body 17 can be decreased in volume by less than 20%, less than 10%, less than 5%, or less than 1% during the injection of the second plastic material 16. Several applications, describing low-pressure injection molding, include, without limitation: US 2012295050, US 2012292823, US 2012291885, US 2013221575, WO 2013126667, WO 2012162245, US 2012294963, US 2012295049.

The process and the apparatus disclosed herein are believed to allow brush manufacturers to create various hollow multi-component plastic articles comprising a hollow body made of a material that is at least partially overmolded with at least one other plastic material or materials, while using relatively simple equipment—and, at the same time, minimizing the risk of having a subsequent plastic material to penetrate into the void inside the hollow body.

While particular embodiments have been illustrated and described herein, various other changes and modifications may be made without departing from the spirit and scope of the invention. Moreover, although various aspects of the invention have been described herein, such aspects need not be utilized in combination. It is therefore intended to cover in the appended claims all such changes and modifications that are within the scope of the invention.

The terms "substantially," "essentially," "about," "approximately," and the like, as may be used herein, represent the inherent degree of uncertainty that may be attributed to any quantitative comparison, value, measurement, or other representation. These terms also represent the degree by which a quantitative representation may vary from a stated reference without resulting in a change in the basic function of the subject matter at issue. Further, the dimensions and values disclosed herein are not to be understood as being strictly limited to the exact numerical values recited. Instead, unless otherwise specified, each such dimension is intended to mean both the recited value and a functionally equivalent range surrounding that value. For example, values disclosed as "65%" or "2 mm" are intended to mean "about 65%" or "about 2 mm," respectively.

The disclosure of every document cited herein, including any cross-referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein—or that it alone, or in any combination with any other reference or references, teaches, suggests, or discloses any such invention. Further, to the extent that any meaning or definition of a term in this document conflicts with any meaning or definition of the same or similar term in a document incorporated by reference, the meaning or definition assigned to that term in this document shall govern.

What is claimed is:

1. A process for making a hollow article by injection molding, the process comprising:
    molding a hollow body of a first plastic material, the hollow body having a wall and a void inside the wall, wherein the wall has at least one vent therethrough, the hollow body comprising at least one flap molded in an area of the wall adjacent to the at least one vent, the flap being molded in a first position in which the vent is open, the flap being hingedly movable from the first position to a second position in which the vent is closed by the flap;
    moving the flap from the first position to the second position with a closing tool, the closing tool comprising a pin, a beam, a bar, a machined or milled structure, or a turned structure;
    injecting a second plastic material through a nozzle located in close proximity to the flap while holding the flap in the second position with the closing tool so that the second plastic material overmolds the flap thereby securing the flap in the second position; and
    at least partially overmolding the hollow body with the second plastic material so that the second plastic material at least partially covers the flap in the second position, wherein the second material is essentially precluded from entering the void inside the hollow body through the vent.

2. The process of claim 1, wherein molding a hollow body includes molding the flap that is sized to fully cover the vent.

3. The process of claim 1, wherein the process further comprises sealing the vent with the flap.

4. The process of claim 3, wherein sealing the vent with the flap comprises an operation including undercut or latch fits.

5. The process of claim 1, wherein moving the flap from the first position to the second position comprises contacting the flap with a closing tool.

6. The process of claim 5, wherein moving the flap from the first position to the second position comprises retaining the flap in the second position with the closing tool.

7. The process of claim 1, wherein molding a hollow body comprises forming the flap that is structured and configured to be flush with an area of the wall surrounding the vent when the flap is in the second position.

8. The process of claim 1, wherein molding a hollow body comprises forming the flap that is structured and configured to overlap a portion of the wall surrounding the vent when the flap is in the second position.

9. The process of claim 1, wherein molding a hollow body comprises gas-assisted injection molding.

10. The process of claim 1, wherein molding a hollow body comprises liquid-assisted injection molding.

11. The process of claim 1, wherein molding a hollow body comprises forming the flap bendable in a bending zone at a bend radius, the bending zone of the flap having a bend thickness, wherein a thickness of the flap in the bending zone divided by the bend radius is less than a maximal allowable strain of the first plastic material in the bending zone.

* * * * *